United States Patent [19]

Toussaint et al.

[11] Patent Number: 5,798,310
[45] Date of Patent: Aug. 25, 1998

[54] GLYPHOSATE COMPOSITIONS AND THEIR USE

[75] Inventors: Marc Emile Toussaint. Corroy-le-Grand; Robert William Mitchell. Overijse. both of Belgium

[73] Assignee: Monsanto Europe S.A., Brussels, Belgium

[21] Appl. No.: 737,903

[22] PCT Filed: Mar. 19, 1996

[86] PCT No.: PCT/EP96/01171

§ 371 Date: Nov. 21, 1996

§ 102(e) Date: Nov. 21, 1996

[87] PCT Pub. No.: WO96/29873

PCT Pub. Date: Oct. 3, 1996

[30] Foreign Application Priority Data

Mar. 24, 1995 [EP] European Pat. Off. ............. 95870025

[51] Int. Cl.$^6$ ..................... A01N 25/30; A01N 57/02; C07C 217/40

[52] U.S. Cl. ..................... 504/206; 564/294

[58] Field of Search .................. 504/206; 564/294

[56] References Cited

U.S. PATENT DOCUMENTS 3,141,905  7/1964  Longley ................. 260/567.6

FOREIGN PATENT DOCUMENTS

| 0 206 537 | 12/1986 | European Pat. Off. | ....... A01N 57/20 |
| 0 274 369 | 7/1988 | European Pat. Off. | ....... A01N 57/20 |
| 0 441 764 | 8/1991 | European Pat. Off. | ....... A01N 57/20 |
| WO 94/02021 | 2/1994 | WIPO | ............. A01N 57/20 |
| WO 94/10844 | 5/1994 | WIPO | ............. A01N 57/20 |

OTHER PUBLICATIONS

Wyrill et al. "Glyphosate Toxicity to Common Milkweed and Hemp Dogbane as Influenced by Surfactants" *Weed Science.* 25(3):275–287, May 1977.

*Primary Examiner*—S. Mark Clardy
*Attorney, Agent, or Firm*—Arnold, White & Durkee

[57] ABSTRACT

The present invention relates to an alkoxylated quaternary ammonium surfactant of Formula I and its utility as a tank mix adjuvant for glyphosate compositions.

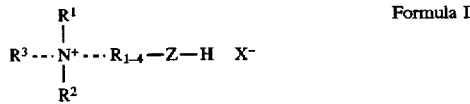

Formula I wherein:
Z is: $-O-(PO)_x-(EO)_y-$
R is:

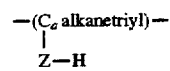

a is an integer from 1 to 8, provided the total number of C atoms is from 3–8
$R^1$ is: $-C_{1-5}$ alkyl
$R^2$ and $R^3$ are defined in the specification and claims.

31 Claims, 3 Drawing Sheets

GLYPHOSATE COMPOSITIONS AND THEIR USE

This application has been filed under 35 USC 371 as the national stage of international application PCT/EP96/01171 filed Mar. 19, 1996.

This invention relates to an agriculturally acceptable glyphosate composition, more particularly to compositions containing a glyphosate herbicide and a surfactant which enhances the herbicidal activity of the glyphosate herbicide. This invention also relates to the use of such compositions to kill or control unwanted and undesired vegetation.

Numerous studies have been made on the effect of additives on the herbicidal action of glyphosate. For example Wyrill and Burnside, Weed Science, Vol. 25 (1977), 275–287, examined solutions containing different classes of surfactant, including polyoxyethylene stearyl methyl ammonium chlorides containing respectively 2 and 15 oxyethylene units. Some classes of surfactant were more effective than others in enhancing the herbicidal effect of glyphosate (used as a solution of the isopropylamine salt), but Wyrill and Burnside concluded that an effective surfactant is a critical component of any glyphosate spray mixture.

Ammonium salts such as ammonium sulphate (Turner and Loader, Weed Research, Vol. 20 (1980), 139–146) and ammonium thiocyanate (U.S. Pat. No. 4,612,034) have also been shown to further enhance the herbicidal activity of glyphosate salt formulations containing surfactants.

EP-A-0 290 416 discloses glyphosate formulations containing alkoxylated amine surfactants, more particularly alkoxylated tallow amine surfactants, and possibly ammonium sulfate. The additives disclosed are said to enhance visibly the glyphosate activity. The formulations disclosed show low irritancy characteristics against ocular tissues, partially due to lower content of surfactant.

U.S. Pat. No. 3,141,905, U.S. Pat. No. 3,123,641 and U.S. Pat. No. 3,123,640 disclose some particular polyoxyalkylated quaternary ammonium surfactants. The use of these types of surfactants in glyphosate compositions is however not disclosed nor suggested. Further, no toxicity or irritancy data in herbicide compositions are disclosed, which could lead the skilled person to test such surfactants with glyphosate herbicide.

British patents No. 1 421 133, 1 462 043, 1 470 618, 1 450 531, 1 453 443, EP-A-0 066 946, WO-87/04595, GB-A-2 113 093, GB-A-2 059 773 and GB-A-2 047 098 disclose quaternary ammonium surfactants in pesticide formulations, but none of them discloses or suggests the compositions of glyphosate herbicide with a quaternary ammonium surfactant(s) which are the subject of the present invention.

European patent No. 0 206 537 discloses the use of Emcol-CC 57, a polypropoxylated quaternary ammonium surfactant, in solid phytoactive glyphosate compositions.

EP-A-0 441 764 discloses herbicidal glyphosate compositions comprising a polypropoxylated quaternary ammonium surfactant having the formula:

wherein —EO— is an ethylene oxide radical and —PO— is a propylene oxide radical. $R^1$ and $R^2$ are each independently an alkyl group having from 1 to 3 carbon atoms; $R^3$ is an alkyl group having from 1 to 3 carbon atoms, a group having the formula $(EO)_m$—H or a group having the formula EO—$(PO)_m$—H; n (in a compound in which $R^3$ is an alkyl group) or n+m (in a compound in which $R^3$ is a group having the formula EO—$(PO)_m$—H), has a value of from 2 to 20; and $X^-$ is a suitable anion and n and m are each independently varying integers. The compositions disclosed are said to be herbicidally effective to a similar extent as were glyphosate compositions comprising ethoxylated fatty amine surfactant considered to be optimum. In addition, such compositions are said to have a low toxicity to fish and to be non-irritant (to skin and eyes).

Herbicidal formulations, however, comprising glyphosate herbicide and a surfactant as specified hereabove, while showing good herbicidal efficacy and a good environmental profile, show a relatively high level of hygroscopicity. This disadvantage is most undesirable, particularly in solid formulations, such as granules, since hygroscopicity of the formulation may result in caking of the granules in the package after an extended exposure to air under unfavorable conditions of humidity; dissolution of the caked solid material in water in the spray tank is then rendered more difficult and takes a longer time. While part of this disadvantage may be overcome by adequate packaging, these, of course, increase the costs of the final product and, hence, the price to the end consumer.

While part of the hygroscopicity is due to formulation ingredients and to the glyphosate salt used in the particular formulation, it has been shown that a major part is due to the surfactant which also constitutes a significant component of the formulation.

There is thus a need for efficient herbicidal glyphosate formulations that show a good environmental profile and that, in addition, show a reduced level of hygroscopicity, compared to the formulations disclosed in EP-A-0 441 764, while having a similar or even better level of bioefficacy.

DETAILED DESCRIPTION OF THE INVENTION

The present invention provides for herbicidal compositions comprising glyphosate herbicide and a quaternary ammonium surfactant having the formula (I):

wherein

R is a group of formula $R^6$—O—$(PO)_{xn}$—$(EO)_{yn}$—H wherein $R^6$ is a $C_1$-$C_8$ alkanetriyl radical, with the proviso that the total C-atom number of the R-group, the oxyalkylene groups being excluded, is of from 3–8 C-atoms;
n is an integer of from 1 to 4, with the understanding that if n is higher than 1, the $R^6$-radicals are the same or different in the individual R-groups;
$R^1$ is a $C_1$-$C_5$ alkyl radical;

$R^2$ is a $C_1$-$C_5$ alkyl radical or a group having the formula $R^4$—O—(PO)$_u$—(EO)$_v$—H wherein $R^4$ is a $C_1$-$C_5$ alkylene radical, or a group (A)$_m$ wherein A represents $A^2$—O—(PO)$_{u'm}$—(EO)$_{v'm}$—H with $A^2$ being selected from $C_1$-$C_8$ alkanetriyl, with the proviso that the total C-atoms number of the A-group, the oxyalkylene groups excluded, is from 3–8 C-atoms;

m is an integer of from 1–4, with the understanding that if m is higher than 1, the $A^2$-groups are the same or different in the individual A-groups.

$R^3$ is a $C_1$-$C_5$ alkyl radical or a group having the formula $R^5$-O—(PO)$_w$—(EO)$_z$—H wherein $R^5$ is a $C_1$-$C_5$ alkylene radical, or a group (B)$_p$ wherein B represents $B^3$-O—(PO)$_{w'p}$—(EO)$_{z'p}$—H with $B^3$ being selected from $C_1$-$C_8$ alkanetriyl, with the proviso that the total C-atom number of the B group, the oxyalkylene groups excluded, is from 3–8 C-atoms;

p is an integer of from 1–4 with the understanding that if p is higher than 1, the $B^3$-groups are the same or different in the individual B-groups.

—EO— means an ethylene oxide radical; and
—PO— means a propylene oxide radical;

$X = x + ex'_n + u + eu'_m + w + ew'_p$ is from 15 to 35; each x, $X'_n$, u, $u'_m$, w and $w'_p$ being an integer;

$Y = y + ey'_n + v + ev'_m + z + ez'_p$ is from 0 to 15; each y, $y'_n$, v, $v'_m$, z and $z'_p$ being an integer;

$ex'_n$ meaning the sum of the propylene oxide radicals of the individual R-groups;

$eu'_m$ meaning the sum of the propylene oxide radicals of the individual A-groups;

$ew'_p$ meaning the sum of the propylene oxide radicals of the individual B-groups;

$ey'_n$ meaning the sum of the ethylene oxide radicals of the individual R-groups;

$ev'_m$ meaning the sum of the ethylene oxide radicals of the individual A-groups;

$ez'_p$ meaning the sum of the ethylene oxide radicals of the individual B-groups; and $x^-$ is a an agriculturally acceptable anion.

The anion is preferably such that the composition is classified both as "non-irritant" when evaluated by a standard test procedure involving dermal and ocular tissue of the rabbit, and as "relatively non-toxic" to fish when evaluated by standard test procedures both hereinafter identified, and not increasing the hygroscopicity of the ammonium moiety.

N,N,N-trialkyl-alkanediyl-bis-polyalkoxyl ammonium chlorides for example can be prepared by alkaline catalytic reaction of N, N-dialkylamino-alkyldiol with alkylenoxide and quaternization thereof with alkylchloride. Other compounds falling under the scope as defined above can be prepared in an analoguous way. It is within the skill of the person skilled in the art to adapt the reaction conditions and starting materials to the final product to be obtained.

Compared to the compositions disclosed in EP-0 441 764, the composition of the present invention containing quaternary ammonium compounds as disclosed hereabove maintains the good environmental profile, with regard to dermal and ocular iritancy and to fish toxicity, shows very good herbicidal activity, and in addition has a reduced hygroscopicity.

As a result, it is now possible to prepare herbicidal glyphosate formulations that have an environmental profile similar to the one of the formulations disclosed in EP-A-0 441 764, while being at least as efficient as same, though eliminating the need for special and/or costly measures to avoid or reduce the water uptake, such as specific packaging. This, of course, reflects in the end consumer price and simplifies the handling, particularly of the solid formulations.

It has also been noticed that the surfactants corresponding to the above formula allow for an easy formulation, particularly of solid compositions, and make it possible to formulate compositions with a high loading of active material.

Among the above quaternary ammonium surfactants, preferred are the surfactants having the formula (II):

wherein
$R^1$ is a $C_1$-$C_5$ alkyl radical;
$R^2$ is a $C_1$-$C_5$ alkyl radical, or a group $R^4$-O—(PO)$_u$—(EO)$_v$—H, $R^4$ being a $C_1$-$C_5$ alkylene group;
$R^3$ is $C_1$-$C_5$ alkyl radical, or a group $R^5$-O—(PO)$_w$—(EO)$_z$—H, $R^5$ being a $C_1$-$C_5$ alkylene group;
$R^7$ being CH—O—(PO)$_{x'n}$—(EO)$_{y'n}$—H;
n being an integer of from 1–4;
$X = x + ex'_n + u + w$ being from 15–35;
$Y = y + ey'_n + v + z$ being from 0–15;
$ex'_n$ meaning the sum of the propylene oxide radicals of $(R^7)$n;
$ey'_n$ meaning the sum of the ethylene oxide radicals of $(R^7)$n;
each x, x', u, w, y, y', v, z being an integer; and
$X^-$ is an agriculturally acceptable anion.

The number of propylene oxide units of the quaternary ammonium symbolized hereabove is preferably in the range from 15 to 30 as the advantages of this invention are more pronounced in that range. More particularly, if there are some ethylene oxide units on the quaternary ammonium compound, the propylene oxide units are preferably between 15 and 30, more particularly about 20.

Herein, the term "glyphosate herbicide" means N-phosphonomethylglycine (glyphosate) and any form or derivative of glyphosate which in aqueous solution provides glyphosate anions. Suitable cations may also be present. Examples of such suitable cations are alkali metal cations, for instance sodium and potassium, and ammonium, diammonium and substituted ammonium cations. The latter include cations derived from primary or secondary amines such as isopropylamine or dimethylamine, and from diamines such as ethylenediamine.

Other examples of agriculturally acceptable salts of glyphosate are the trimethyl sulfonium salt of glyphosate, or aminoguanidine salts as disclosed in EP-A-0 088 180. Because glyphosate has more than one replaceable hydrogen atom, mono- and di-alkali metal salts are possible, as well as mixtures of such salts.

Quaternary ammonium compounds available in practice are not necessarily pure compounds in the sense of consisting of a single molecular species. In any particular instance, several different compounds where x, x', y, y', u, u', v, v', w, w', z and z' vary over a narrow range will normally be present, so that the values of x, x', y, y', u, u', v, v', w, w', z and z'mentioned above are understood as average values. It is known to the person skilled in the art that during the propoxylation process or ethoxylation process, the propylene oxide and ethylene oxide radicals, respectively, are distributed over the reactive sites in an essentially even way. That means that, in average, the individual propylene oxide chains and ethylene oxide chains, respectively, of an compound have essentially the same length. Some minor differences only in chain length may be due to the difference in reactivity of the sites. As an example, some compounds comprise primary and secondary reactive carbon sites, which may lead to a difference of one alkoxy unit between those sites.

The anion symbolized as X⁻ in the Formula symbolizing a quaternary ammonium compound used in a composition of the invention can be for example a halide ion, for instance chloride or bromide, phosphate, or methylsulphate, or ethylsulphate, or a glyphosate ion. Other suitable anions include acetate, lactate, dimethyl phosphate or polyalkoxylated phosphate and the like.

In the compositions of this invention, the weight ratio of glyphosate (expressed as glyphosate acid equivalent) to the quaternary ammonium compound can vary over a considerable range, for example from about 1:5 to about 10:1. The optimum ratio will vary according to the manner in which the herbicidal composition is applied, the weed species to be treated, and the particular quaternary ammonium compound selected, but is normally within the range from about 1:2 to about 5:1, for example about 1:1, about 2:1, or about 4:1.

A composition of the invention can be a liquid aqueous concentrate intended to be diluted with water to form a spray solution for the actual herbicidal application. A liquid concentrate will normally contain at least 50 grams glyphosate acid equivalent per liter, and preferably at least 100 g/l. Compositions of the invention may include a significant amount of an agriculturally-acceptable inorganic ammonium salt such as ammonium sulphate, in addition to the glyphosate and quaternary ammonium compound. Liquid concentrates without such an inorganic ammonium salt can contain up to 450 g/l or more, for example 300–450 g/l, glyphosate acid equivalent when the glyphosate is present as a salt having a high solubility, for example the isopropylamine salt. In liquid concentrates containing an inorganic ammonium salt (for example ammonium sulphate in an amount of from 100 to 500 g/l), the maximum amount of glyphosate which can be accommodated is less, and may be, for example, about 150 g/l glyphosate acid equivalent. Such liquid concentrate may require, depending on the loading, the presence of a compatibility agent, which the man skilled in the art will find without undue burden of experimentation.

In another form, the composition of the invention is a solid, for example a free-flowing particulate, granular solid or compressed into tablets or briquets of any desired size and shape. The term "solid" as employed herein includes granular, particular, wettable powder, water soluble and water dispersible formulations, or mixtures thereof. Typically such solids are dry. Such dry compositions will usually contain not more than 5% and preferably not more than 1% by weight of water.

In a solid composition, glyphosate is preferably present as an alkali metal salt such as a sodium or potassium salt, or as an ammonium salt and in some cases the isopropylamine salt. The surfactant used in the compositions of the invention particularly allows for relatively high concentrations of glyphosate herbicide in the solid formulation.

Optionally solid compositions may be formulated to include a water-soluble inert carrier, and for this purpose ammonium sulphate, ammonium thiocyanate, or ammonium phosphate are particularly suitable. The weight ratio of glyphosate (expressed as glyphosate acid equivalent) to quaternary ammonium compound in such compositions will be within the general range mentioned above. The amount of water-soluble inert carrier is not critical, and in the case of ammonium sulphate, the amount may, for example, range from 20% to 80% of the total weight of the composition. Solid compositions can be made, for example by spray drying an aqueous solution of the components, by dry-blending the ingredients in conventional blending apparatus, or by extrusion blending whereby a granular product is obtained in an essentially single operation. In a preferred method, an alkali metal or ammonium salt of glyphosate is produced in situ in an extruder as known in the art. It has been found that the product obtained by radial extrusion has better dissolution characteristics in water compared to a product obtained by frontal extrusion.

The compositions of the invention can be diluted as spray solutions which may be applied by spraying for example. In these solutions, the concentration of glyphosate is selected according to the volume per unit area of spray solution to be used and the desired rate of application of glyphosate per unit area. For example, conventional spraying is done at 100–600 liters of spray solution per hectare, and the rate of application of glyphosate is typically 0.125 to 3 kg of glyphosate acid equivalent per hectare. In controlled drop spraying, the rate of application of glyphosate per hectare will normally be in the same range, but the volume of spray solution per hectare will be considerably less, perhaps 15–50 liters per hectare. Spray solutions for controlled drop spraying are therefore more concentrated than those used in conventional spraying. In spray solutions containing inorganic ammonium salts in addition to the glyphosate and quaternary ammonium compound, the amount of inorganic ammonium salt which can be included may be, for example, up to 10 times the weight of glyphosate acid equivalent.

Spray solution compositions can be prepared by diluting liquid concentrates with water or dissolving solid compositions in water as described above, or by tank mixing the separate components of the compositions.

Compositions of the invention can optionally contain other components, preferably those and in amounts that do not have a substantial adverse effect on the resulting composition as to irritancy and toxicity and hygroscopicity. These additional components may include anti-freeze agents such as ethylene glycol, polyethylene or polypropylene glycols and/or glycerol. Other examples of additional components are dyes, thickening agents, anti-foam agents, for instance silicone-based anti-foam agents, agents suitable for pH adjustment to optimize herbicidal efficacy and compatibility or stability of the composition, and certain surfactants, for instance non-ionic surfactants such as polyoxyethylene ethers or esters, sugar ethers and sorbitan esters. The compositions of the invention may also comprise one or more herbicides, themselves preferably having low or no irritancy and relatively low toxicity.

The surfactants as disclosed herein can also be used to prepare tank mix adjuvants for glyphosate spray dilutions, that may additionally comprise anti-freeze agents, dyes, thikening agents, anti-foam agents and/or co-surfactants.

Some salts of the quaternary ammonium cations with chloride anions shown in Table 1 following were used to prepare compositions in turn used in investigating their potentiating effect on the herbicidal action of glyphosate.

TABLE 1

| Quaternary ammonium cation with chloride anion according to formula II: | | | | | |
|---|---|---|---|---|---|
| N* | R₁ | R₂ | R₃ | n | X | Y |
| 1 | CH₃ | CH₃ | CH₃ | 1 | 20.0 | 0 |
| 2 | CH₃ | CH₃ | CH₃ | 1 | 30.0 | 0 |
| 3 | CH₃ | CH₃ | CH₃ | 1 | 20.0 | 2 |
| 4 | CH₃ | CH₃ | CH₃ | 1 | 20.0 | 4 |
| 5 | CH₃ | $R_2 = R_3 = CH_2-CH_2-O-(PO)_{a/w}-H$ | | | 1 | 18.0 | 0 |
| 6 | CH₃ | $R_2 = R_3 = CH_2-CH_2-O-(PO)_{a/w}-H$ | | | 1 | 28.0 | 0 |

TABLE 1-continued

Quaternary ammonium cation with chloride anion according to formula II:

| N* | $R_1$ | $R_2$ | $R_3$ | n | X | Y |
|---|---|---|---|---|---|---|
| 7 | $CH_3$ | $CH_3$ | $CH_2-CH-CH_3$<br>        \|<br>        $O(PO)_nH$ | 4 | 20.0 | 0 |
| 8 | $CH_3$ | $CH_3$ | $CH_2-CH-CH_3$<br>        \|<br>        $O(PO)_nH$ | 4 | 31.0 | 0 |

EXAMPLE 1

The surfactants exemplified in Table I were tested in order to determine their hygroscopicity, in comparison with a control. The control is a surfactant as disclosed in EP-A-O 441 764 wherein $R^1=R^2=R^3=CH_3$ and n=8, and was among the most preferred surfactants for reasons of bioefficacy enhancement and environmental profile.

First, the samples were dried in an oven to a water content assayed by the Karl-Fisher (K-F) titration method below 3%. Then the samples were submitted to controlled condition, in a climatic chamber, controlled at 70% RH and 20° C. The water content was assayed again after 18 hours (K-F 18 h) and 90 hours (K-F 90 h) residence time in the climatic chamber.

The actual water uptake at 18 h and 90 h was calculated by substracting the water content assayed before the introduction of the samples in the chamber, from the water content assayed at 18 h and 90 h, respectively. The results are presented in Table II following and in FIG. 1, expressed in % by weight.

Figure 1:
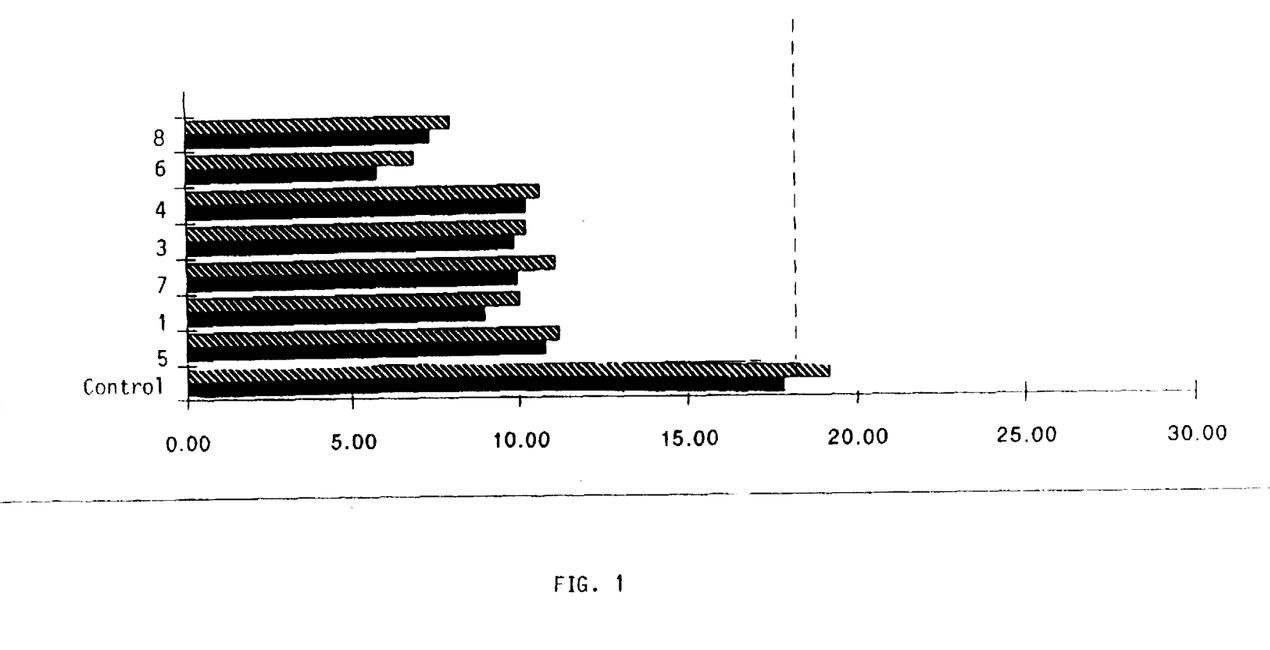
FIG. 1 shows reduced hygroscopicity of the compositions of the invention compared to the control known from prior art herbicidal glyphosate compositions.

As it appears clearly from Table II and FIG. 1, the surfactants for use in the compositions of the invention show a much reduced hygroscopicity when compared to the control known from prior art herbicidal glyphosate compositions.

TABLE II

| Sample | K-F | K-F (18 h) | K-F (90 h) | Water uptake 18 h | Water uptake 90 h |
|---|---|---|---|---|---|
| Control | 2.27 | 20.12 | 21.49 | 17.85 | 19.22 |
| 5 | 0.17 | 10.98 | 11.38 | 10.81 | 11.21 |
| 1 | 1.55 | 10.52 | 11.58 | 8.97 | 10.03 |
| 7 | 0.25 | 10.20 | 11.37 | 9.95 | 11.12 |
| 3 | 1.35 | 11.21 | 11.58 | 9.86 | 10.23 |
| 4 | 1.29 | 11.51 | 11.94 | 10.22 | 10.65 |
| 6 | 0.14 | 5.93 | 7.01 | 5.79 | 6.87 |
| 8 | 0.12 | 7.50 | 8.09 | 7.38 | 7.97 |

EXAMPLE 2

7000.0 g of glyphosate monoammonium salt (86.6% a.e.) and 35.0 g PG2028 defoamer were loaded in a Glatt VG-25 mixer. The material was mixed at a blade rotation speed of 150 rpm (refiner at 3000 rpm). 1610.0 g of a surface active material comprising 90% active material of the formula corresponding to the formula of compound N.1 were slowly added into the mixer under mixing conditions as described above. Thereafter 368.0 g of polyoxyethylene (20 EO) sorbitan monolaurate (99%) were slowly added into the mix, under mixing conditions. After completion of the surfactant addition, the mixer content was further blended for about 2 minutes in order to obtain a free-flowing white blend, and then 37.0 g of water were slowly added under mixing in order to obtain an extrudable dough.

The dough-like material obtained in the mixer was extruded in a Fuji-Paudal EXDS-60 extruder through a 1 mm radial screen. The extrudates were then forwarded to a fluid bed dryer and dried to a water content of about 0.4–0.5%.

The final granular composition corresponds to the following (in parts by weight):

Momoammonium salt of glyphosate (86.6% a.e.) 78.6
surfactant N.1 16.4
sorbitan ester (20 EO) 4.1
PG 2028 defoamer 0.4
water 0.5
TOTAL 100

EXAMPLE 3

700 g of surfactant N.1 and 73 g water were loaded into a Hobart mixer and blended in a satisfactory way. Then, 2246.0 g of glyphosate monoammonium salt (86.6% a.e.) were slowly added under mixing. Mixing was extended for about 5 further minutes, thus obtaining an extrudable dough-like material.

The material obtained was extruded and dryed as in Example 2 hereabove.

The final composition was as follows (in parts by weight):

Momoammonium salt of glyphosate (86.6% a.e.) 77.7
surfactant N.1 21.8
water 0.5
TOTAL 100

EXAMPLE 4

The solid composition of Example 3 was submitted to tests according to corresponding OECD guidelines.

(i) Eye irritancy

The potential eye irritant and/or corrosive effects of the composition of Example 3 were evaluated on New Zealand White rabbits. Each of six rabbits received a 0.0700 g (0.1 ml volume equivalent) dose of the test composition in the conjunctival sac of the right eye. The contralateral eye of each animal remained untreated and served as a control. Test and control eyes were examined for signs of irritation for up to 10 days following dosing.

The test composition was ground in a mortar and pestle and passed through a No. 40 mesh sieve. The weight of processed test composition that occupied a volume of 0.1 ml (0.0700 g) was then determined and utilized for dose administration.

Exposure to the test composition produced iritis in 6/6 test eyes at the 1 hour scoring interval which resolved completely in all animals by the 72 hour scoring interval. Conjunctivitis (redness, swelling and discharge) was noted in 6/6 test eyes at the 1 hour scoring interval. The conjunctival irritation generally diminished during the remainder of the test period and resolved completely in all animals by study day 10. Additional ocular findings included sloughing of the corneal epithelium, which was noted in 1/6 test eyes.

Under the conditions of this test, the test composition is considered to be moderately irritating to the ocular tissue of the rabbit. The EEC classification based on ocular lesions would be "not classified" for opacity, iritis, conjunctival redness and conjunctival swelling.

(ii) Acute Toxicity to Daphnia

The exposure of Daphnia magna was conducted under flow-through conditions in a modified proportional vacuum-siphon diluter system based on the original design by Mount and Brungs (1967).

A solution of the test composition was prepared to provide the nominal test concentrations of 6.25, 12.5, 25.0, 50.0, 100 and 200 mg (whole material)/l.

Survival of daphnids was monitored daily and any dead removed. Any abnormalities in the behavior or physical appearance of daphnids were also noted.

Based on results of the test, the 48-hour $EC_{50}$ value (the concentration of the test composition estimated to result in immobilization or death to 50% of the test population at the specified time), the slope of the concentration/mortality response curve, and the 95 percent confidence limits were calculated. The $EC_{50}$ value was estimated by a computer program (Wheat, 1989) using the following statistical methods: moving average angle, probit, logit, and non-linear interpolation. Confidence limits for $EC_{50}$ values determined by non-linear interpolation were calculated by binomial probability. The method selected for reporting the test results was determined by the characteristics of the data, i.e., the presence or absence of 0-percent and 100-percent mortality and the number of concentrations in which mortalities between 0 and 100 percent occured (Stephan, 1977).

Mortality of the daphnia exposed for 48 hours to the test composition ranged from 0 percent at test concentrations $\leq 53.8$ to 55 percent at 226 mg/l. Mortality was zero percent in the dilution water control. The 48-hour $EC_{50}$ was 214 mg/l with 95 percent confidence limits of 173 and 306 mg/l. The slope of the concentration/mortality response curve was calculated to be 5.27 using the probit method. The no-observed-effect concentration (NOEC) was 53.8 mg/l based on a lack of mortality and absence of sublethal effects at this test concentration and all lower test concentrations.

Initial alkalinity, hardness and conductivity of the dilution water as measured in the control container were 28 mg/l as $CaCO_3$, 54 mg/l as $CaCO_3$ and 462 µmhos/cm respectively. At test termination, alkalinity, hardness and conductivity of the dilution water as measured in the control container were 36 mg/l as $CaCO_3$, 86 mg/l as $CaCO_3$ and 470 µmhos/cm. The mean test temperature during the 48-hour exposure was 20.5±0.1° C. and ranged from a minimum of 20.3° C. to a maximum of 21.0° C. Initial dissolved oxygen concentrations in the control and all six test solutions ranged from 8.3 to 8.5 mg/l (93 to 96 percent of saturation). The dissolved oxygen concentrations in the control and all test solutions ranged from 8.2 to 8.4 mg/l (92 to 94 percent of saturation) for the remainder of the test. The pH of the test solutions was affected by the presence of the test compositions with pH decreasing with increasing test substance concentrations. The pH in the control replicates ranged from 7.8 to 7.9 during the test. The pH of the test solutions at test initiation ranged from 5.7 to 7.6 and remained from 5.6 to 7.6 throughout the test.

(iii) Acute Toxicity to Rainbow Trout

A 96-hour static toxicity test was conducted on the test composition with rainbow trout (*Oncorhynchus mykiss*). A dilution water control and six concentrations of the test composition (10.0, 50.2, 100, 250, 500, and 1000 mg/l) were tested. Due to the solubility of the test compound, test solutions were prepared by adding the appropriate amount (grams) of test substance directly into each test chamber and stirring.

The test was conducted in 54-l glass aquaria containing 50 l of dilution water. The dilution water was treated town water with a initial hardness of 62 mg/l as $CaCO_3$, and alkalinity of 8 mg/l as $CaCO_3$, and specific conductivity of 453 micomhos/centimeter. The test containers were positioned in a water bath to maintain test temperature at 12°±10° C. and under fluorescent lighting providing a photoperiod of 16 hours light and 8 hours darkness. Light intensities as measured at test solution level ranged from 4.7 to 7.0 µE/m₂/s (approximately 392 to 583 lux). Following addition of the test composition to the test containers, fish were added by twos until a total of 10 fish per concentration was attained. Juvenile rainbow trout used in the test ranged from 40 to 55 millimeters in standard length (average±standard deviation—46.1±4.4 mm) and 0.66 to 2.58 grams (g) in wet weight (average±standard deviation—1.35±0.53 g) as determined from control fish at test termination. Loading in the test was calculated to be 0.27 g/l.

After 96 hours of exposure, mortality of rainbow trout exposed to the test composition was zero percent at concentrations 10.0, 50.2, 100 and 250 mg/l. There was ten percent mortality at 500 mg/l and 100 percent at the high concentration of 1000 mg/l. The control had ten percent mortality. The $LC_{50}$ was calculated by the binomial method to be 658 mg/l.

Initial dissolved oxygen concentrations ranged from 8.8 to 9.8 mg/l ($\geq 80$ percent of saturation) and remained $\geq 6.8$ mg/l ($\geq 62$ percent of saturation) throughout the test. The addition of the test composition affected the pH of the dilution water (i.e. as the test composition concentrations increased, pH decreased). The pH of the controls and the test treatments ranged from 7.4 to 4.1 at test initiation and from 6.9 to 4.0 at test termination. Test temperature was maintained at 10.8° to 12.1° C.

EXAMPLE 5

Tank mixes of several surfactants according to the invention with the isopropylamine salt of glyphosate were evaluated in a greenhouse trial, the weight ratio of glyphosate a.e. to surfactant being 2/1. Such tank mixes were compared with the commercial formulation Roundup® (360 g/l a.e. as the isopropylamine salt of glyphosate and 180 g/l ethoxylated tallow amine surfactant) and with a tank mix of the isopropylamine salt of glyphosate with a surfactant according to EP-A-0 441 764 (considered optimum) wherein $R^1=R^2=R^3=CH_3$ and n=8, in a 2/1 ratio. Glyphosate herbicide was applied at a rate of 1080 g a.e./ha in all instances.

A warm season weed species (ECHCG-*Echinochloa erecta*) was grown from seed in a growth-room at a temperature of 18° C. during the night and 24° C. during the day. A cold season weed species (BRSNW-*Brassica napus*) was grown from seed in a growth-room at the temperature of 12° C. during the night and 18° C. during the day. All plants were grown under 50% and 75% RH during the night and the day, respectively.

Before spraying, pots were selected for uniformity as far as possible, and atypical examples were discarded. Spray solutions were applied with a field equipment (spraying system-R&D Sprayers Inc), calibrated to deliver spray solution at a rate equivalent to 200 l/ha with Teejet nozzles 8002. All replicate pots (3–5 replicates per species, per treatment) were sprayed with one pass of the sprayer.

After spraying, the plants were transferred to a greenhouse (about 20° C.) and control pots were placed at random among treated pots.

Assessment of "% phytotoxicity" were made by comparison with untreated controls on an arbitrary scale from 0 to 100%, where 0 means no visible effect and 100% means death of all plants.

Figure 2:
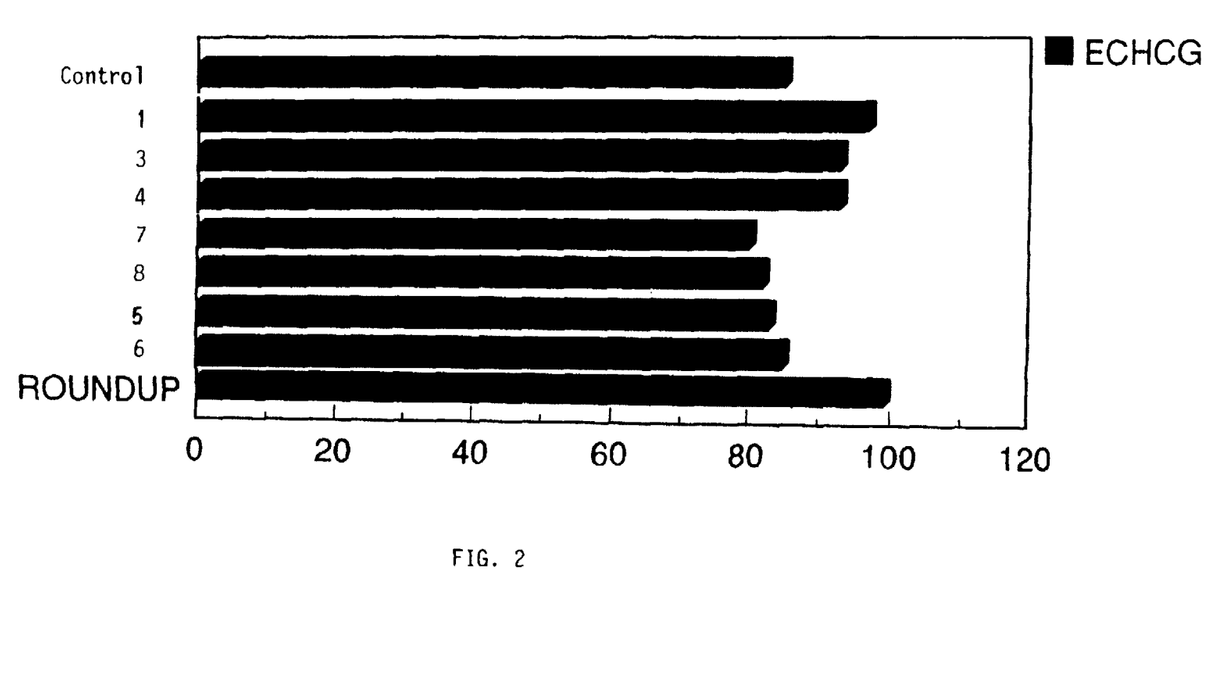
FIG. 2 shows the percent phytotoxicity at 26 DAT to *Echinochloa erecta* (ECHCG).

Assessments were made at several intervalls (DAT: days after treatment). The results are respresented in the form of a graph. FIG. 2 represents the percent phytotoxicity at 26 DAT to ECHCG, and FIG. 3 represents the percent phytotoxicity to BRSNW at 38 DAT.

Figure 3:
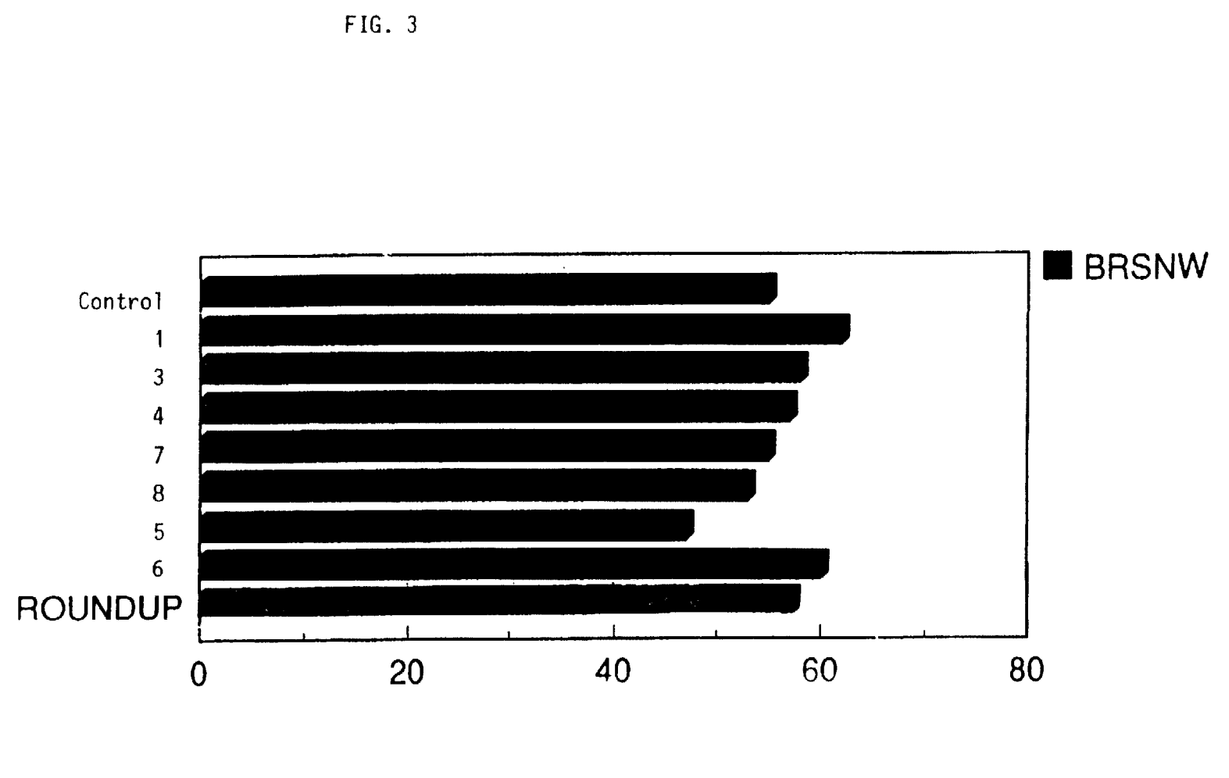
FIG. 3 shows the percent phytotoxicity to *Brassica napus* (BRSNW) at 38 DAT.

It appears from FIGS. 2 and 3 that the tank mixes according to the present invention perform similarly to the tank mix according to EP-0 441 764 and almost reach the performance of Roundup®.

We claim:

1. A tank mix adjuvant for use with glyphosate herbicide, comprising a quaternary ammonium compound having the Formula I:

wherein n is an integer of from 1 to 4;

Z is —O—(PO)$_x$—(EO)$_y$—;

R is (C$_a$ alkanetriyl)—Z—H;

a is an integer of from 1 to 8, provided that the total number of carbon atoms in all of the C$_a$ alkanetriyl groups is from 3 to 8;

R$^1$ is a C$_{1-5}$ alkyl;

R$^2$ and R$^3$ are independently a C$_{1-5}$ alkyl or R$^4$—Z—H;

R$^4$ is a C$_{1-5}$ alkylene or (A)$_m$;

m is an integer of from 1 to 4;

A is (C$_b$ alkanetriyl)—Z—H;

b is an integer of from 1 to 8, provided that the total number of carbon atoms in all of the C$_b$ alkanetriyl groups is from 3 to 8;

PO is a propylene oxide radical;

EO is an ethylene oxide radical;

x and y are integers, provided that x and y may be different at each occurrence in Formula I, such that the total number of propylene oxide radicals in Formula I is 15–35, and the total number of ethylene oxide radicals in Formula I is 0–15; and X$^-$ is an agriculturally acceptable anion.

2. The tank mix adjuvant of claim 1, further comprising an agent selected from the group consisting of anti-freeze agents, dyes, thickening agents, anti-foam agents, co-surfactants and co-herbicides.

3. A composition comprising glyphosate herbicide in its acid form or in a salt form and a quaternary ammonium compound having the Formula I:

wherein n is an integer of from 1 to 4;

Z is —O—(PO)$_x$—(EO)$_y$—;

R is (C$_a$ alkanetriyl)—Z—H;

a is an integer of from 1 to 8, provided that the total number of carbon atoms in all of the C$_a$ alkanetriyl groups is from 3 to 8;

R$^1$ is a C$_{1-5}$ alkyl;

R$^2$ and R$^3$ are independently a C$_{1-5}$ alkyl or R$^4$—Z—H;

R$^4$ is a C$_{1-5}$ alkylene or (A)$_m$;

m is an integer of from 1 to 4;

A is (C$_b$ alkanetriyl)—Z—H;

b is an integer of from 1 to 8, provided that the total number of carbon atoms in all of the C$_b$ alkanetriyl groups is from 3 to 8;

PO is a propylene oxide radical;

EO is an ethylene oxide radical;

x and y are integers, provided that x and y may be different at each occurrence in Formula I, such that the total number of propylene oxide radicals in Formula I is 15–35, and the total number of ethylene oxide radicals in Formula I is 0–15; and X$^-$ is an agriculturally acceptable anion.

4. A composition according to claim 3 wherein, in the formula, R$^1$, R$^2$ and R$^3$ are methyl, and n=1.

5. A composition according to claim 3 wherein the total number of propylene oxide radicals is from 15–30.

6. A composition according to claim 3 wherein the total number of propylene oxide radicals is about 20.

7. A composition according to claim 3 wherein the total number of ethylene oxide radicals is 0.

8. A composition according to claim 3, wherein the weight ratio of glyphosate (expressed as glyphosate acid equivalent) to the quaternary ammonium compound is in the range from 1:5 to 10:1.

9. A composition according to claim 3, which is a solid composition containing at least 40% by weight glyphosate (expressed as glyphosate acid equivalent) as an alkali metal or ammonium salt of glyphosate.

10. A composition according to claim 3, which includes an ammonium salt as carrier material.

11. A composition according to claim 3 comprising an ammonium salt as a water soluble inert support, in an amount of from 10% to 60% of the total weight of the composition.

12. A composition according to claim 3 further comprising an agent selected from the group consisting of anti-freeze agents, dyes, thickening agents, anti-foam agents, co-surfactants and co-herbicides.

13. A composition according to claim 3 wherein the quaternary ammonium compound corresponds to the formula II:

wherein n is an integer of from 1 to 4;

Z is —O—(PO)$_x$—(EO)$_y$—;

R$^1$ is a C$_{1-5}$ alkyl;

R$^2$ and R$^3$ are independently a C$_{1-5}$ alkyl or R$^4$ —Z—H;

R$^4$ is a C$_{1-5}$ alkylene;

R$^7$is CH—Z—H;

PO is a propylene oxide radical;

EO is an ethylene oxide radical;

x and y are integers, provided that x and y may be different at each occurrence in Formula II, such that the total number of propylene oxide radicals in Formula II is 15–35, and the total number of ethylene oxide radicals in Formula II is 0–15; and X$^-$ is an agriculturally acceptable anion.

14. A composition according to claim 13 wherein, in the formula, R$^1$, R$^2$ and R$^3$ are the same or different and represent a C$_1$-C$_5$ alkyl radical.

15. A composition according to claim 3, wherein the weight ratio of glyphosate (expressed as glyphosate acid equivalent) to the quaternary ammonium compound is in the range from 1:2 to 5:1.

16. A composition according to claim 3, wherein, in the formula, $R^1$, $R^2$ and $R^3$ are the same or different and represent a $C_1$-$C_5$ alkyl radical, the total number of propylene oxide radicals is from 15-30, the total number of ethylene oxide radicals is 0, and the weight ratio of glyphosate (expressed as glyphosate acid equivalent) to the quaternary ammonium compound is in the range from 1:5 to 10:1.

17. A method of killing a plant or regulating its growth, comprising administering to a plant a composition in a herbicidally effective amount or a plant growth regulating effective amount, the composition comprising:

glyphosate herbicide in its acid form or in a salt form and a quaternary ammonium compound having the Formula I:

wherein n is an integer of from 1 to 4;

Z is —O—(PO)$_x$—(EO)$_y$—;

R is (C$_a$ alkanetriyl)—Z—H;

a is an integer of from 1 to 8, provided that the total number of carbon atoms in all of the C$_a$ alkanetriyl groups is from 3 to 8;

$R^1$ is a $C_{1-5}$ alkyl;

$R^2$ and $R^3$ are independently a $C_{1-5}$ alkyl or $R^4$—Z—H;

$R^4$ is a $C_{1-5}$ alkylene or (A)$_m$;

m is an integer of from 1 to 4;

A is (C$_b$ alkanetriyl)—Z—H;

b is an integer of from 1 to 8, provided that the total number of carbon atoms in all of the C$_b$ alkanetriyl groups is from 3 to 8;

PO is a propylene oxide radical;

EO is an ethylene oxide radical;

x and y are integers, provided that x and y may be different at each occurrence in Formula I, such that the total number of propylene oxide radicals in Formula I is 15-35, and the total number of ethylene oxide radicals in Formula I is 0-15; and X$^-$ is an agriculturally acceptable anion.

18. A method according to claim 17 wherein the quaternary ammonium compound corresponds to the Formula II:

wherein n is an integer of from 1 to 4;

Z is —O—(PO)$_x$—(EO)$_y$—;

$R^1$ is a $C_{1-5}$ alkyl;

$R^2$ and $R^3$ are independently a $C_{1-5}$ alkyl or $R^4$—Z—H;

$R^4$ is a $C_{1-5}$ alkylene;

$R^7$ is CH—Z—H;

PO is a propylene oxide radical;

EO is an ethylene oxide radical;

x and y are integers, provided that x and y may be different at each occurrence in Formula II, such that the total number of propylene oxide radicals in Formula II is 15-35, and the total number of ethylene oxide radicals in Formula II is 0-15; and X$^-$ is an agriculturally acceptable anion.

19. A method according to claim 17, wherein, in the formula, $R^1$, $R^2$ and $R^3$ are the same or different and represent a $C_1$-$C_5$ alkyl radical, the total number of propylene oxide radicals is from 15-30, the total number of ethylene oxide radicals is 0, and the weight ratio of glyphosate (expressed as glyphosate acid equivalent) to the quaternary ammonium compound is in the range from 1:5 to 10:1.

20. A method according to claim 17 wherein, in the formula, $R^1$, $R^2$ and $R^3$ are the same or different and represent a $C_1$-$C_5$ alkyl radical.

21. A method according to claim 17 wherein, in the formula, $R^1$, $R^2$ and $R^3$ are methyl, and n=1.

22. A method according to claim 17 wherein the total number of propylene oxide radicals is from 15-30.

23. A method according to claim 17 wherein the total number of propylene oxide radicals is about 20.

24. A method according to claim 17 wherein the total number of ethylene oxide radicals is 0.

25. A method according to claim 17, wherein the weight ratio of glyphosate (expressed as glyphosate acid equivalent) to the quaternary ammonium compound is in the range from 1:5 to 10:1.

26. A method according to claim 17, where the composition is a solid composition containing at least 40% by weight glyphosate (expressed as glyphosate acid equivalent) as an alkali metal or ammonium salt of glyphosate.

27. A method according to claim 17, where the composition includes an ammonium salt as carrier material.

28. A method according to claim 17, where the composition further comprises an ammonium salt as a water soluble inert support, in an amount of from 10% to 60% of the total weight of the composition.

29. A method according to claim 17, whether the composition further comprises an agent selected from the group consisting of anti-freeze agents, dyes, thickening agents, anti-foam agents, co-surfactants and co-herbicides.

30. A method according to claim 17, wherein the weight ratio of glyphosate (expressed as glyphosate acid equivalent) to the quaternary ammonium compound is in the range from 1:2 to 5:1.

31. A method according to claim 17, where the composition is applied to narrowleaf or broadleaf vegetation in a rate of between 0.125 and 3 kg glyphosate acid equivalent per hectare.

* * * * *

UNITED STATES PATENT AND TRADEMARK OFFICE
CERTIFICATE OF CORRECTION

PATENT NO. : 5,798,310
DATED : August 25, 1998
INVENTOR(S) : Toussaint et al.

It is certified that error appears in the above-identified patent and that said Letters Patent is hereby corrected as shown below:

Column 14, line 48 (claim 29), delete "whether" and insert therefor --wherein--.

Signed and Sealed this

Sixteenth Day of March, 1999

Attest:

Attesting Officer

Q. TODD DICKINSON

Acting Commissioner of Patents and Trademarks